United States Patent [19]

Bruzzese et al.

[11] Patent Number: 6,143,726
[45] Date of Patent: Nov. 7, 2000

[54] COMPLEXES OF N'-DIMETHYLAMINOACETYLPARTRICIN A DIMETHYLAMINOETHYLAMIDE, OR THE SALTS THEREOF, AND CHOLESTEROL 3-SULPHATE

[75] Inventors: Tiberio Bruzzese; Giovanni Mozzi, both of Milan, Italy

[73] Assignee: Quatex N.V., Curaçao, Netherlands

[21] Appl. No.: 09/147,509

[22] PCT Filed: Jul. 2, 1997

[86] PCT No.: PCT/EP97/03465

§ 371 Date: Jan. 12, 1999

§ 102(e) Date: Jan. 12, 1999

[87] PCT Pub. No.: WO98/02168

PCT Pub. Date: Jan. 22, 1998

[30] Foreign Application Priority Data

Jul. 12, 1996 [IT] Italy .................................. MI96A1449

[51] Int. Cl.$^7$ ..................................................... A61K 31/70
[52] U.S. Cl. .............................. 514/31; 536/6.5; 536/16.8
[58] Field of Search ................................ 514/31; 536/6.5, 536/16.8

[56] References Cited

U.S. PATENT DOCUMENTS

| 4,822,777 | 4/1989 | Abra | 574/31 |
| 5,296,597 | 3/1994 | Bruzzese et al. | 594/106 |

*Primary Examiner*—Elli Peselev
*Attorney, Agent, or Firm*—Oblon, Spivak, McClelland, Maier & Neustadt, P.C.

[57] ABSTRACT

A complex containing N'-dimethylaminoacetylpartricin A dimethylaminoethylamide, as a salt or as the free base, and cholesterol 3-sulphate, in a molar ratio between 1:0.5 and 1:10, respectively.

8 Claims, No Drawings

COMPLEXES OF N'-DIMETHYLAMINOACETYLPARTRICIN A DIMETHYLAMINOETHYLAMIDE, OR THE SALTS THEREOF, AND CHOLESTEROL 3-SULPHATE

The present invention refers to the complexes forming between N'-dimethylaminoacetylpartricin A dimethylaminoethylamide, (SPA-S-752), or the salts thereof, and cholesterol 3-sulphate, and the pharmaceutical compositions containing them, useful in the treatment of systemic mycoses. Examples of a salt are the diaspartate (SPA-S-753), the diascorbate (SPA-S-843) and any other salt that is pharmaceutically acceptable.

At present, the request for antifungal agents is pressing owing to the diffusion of systemic mycoses in patients with debilitating diseases such as cancer, and in immunodeficiency conditions, such as HIV III infections (AIDS). Organ grafting too, in conjunction with the subsequent, indispensable immunosuppressive treatments, is one of the causes of the progressive diffusion of the often lethal mycotic infections. Systemic mycoses, for example, are found as often as nearly 50% in patients having died of acute leukaemia and following renal transplant. These mycoses are caused by a large number of pathogenic microorganisms of the mould and yeast class (Aspergillus, Candidae, Cryptococcus etc.).

The therapeutic measures so far available to the physician are limited to some substances, none of which effective on all of the infecting species. Availability of new systemic antifungal agents is therefore vital, owing also to the high toxicity of those already available, limiting their use to doses insufficient to cure and inadequate to prevent. These drugs high toxicity requires that they be used in hospital only, during even prolonged hospitalisation (several weeks and months), distressing to the patient and costly for the community.

As for the compound N'-dimethylaminoacetylpartricin A dimethylaminoethylamide diaspartate (henceforth mentioned with code name SPA-S-753), for instance, it is a known synthetic derivative (U.S. Pat. No. 5,298,495, Bruzzese T. et al., 1994) of partricin A, a polyene antibiotic obtained through fermentation of a streptomyces aureofaciens strain. SPA-S-753 presents a toxicity definitely much lower than that of partricin which enables its clinical use, a high water-solubility which permits its parenteral administration, and similar microbiological activity against various fungi (*Candida albicans, Candida parapsilopsis, Candida rusei, Candida tropicalis, Candida guilliermondi, Candida glabrata, Cryptococcus laurentii, Cryptococcus albidus, Cryptococcus neoformans, Saccharomyces cerevisiae, Syncephalastrum racemosum, Trichosporon cutaneum, Trichophytum mentagrophytes, Trichophytum rubrum, Aspergillus niger, Aspergillus fumigatus*) and protozoa (*Trichomonas vaginalis*), attributable to its capacity of interacting with cell membranes (Strippoli V., Simonetti N., Villa A., Bruzzese T.—European Bulletin of Drug Research, 1, 113, 1992 and Strippoli V., Simonetti N., D'Auria F. D., Bruzzese T.—European Bulletin of Drug Research, 3, 71, 1994).

SPA-S-753 toxicity is however not low enough as to allow its use outside close medical supervision in hospital, nor to exclude important side effects. For example, SPA-S-753 intramuscular administration leads to its partial precipitation which has a negative influence on tolerance of the product. Like all other drugs employed in the pathologies in question, the side effects connected with the use of the product might limit the extent of the doses to be administered, with the risk that in certain cases treatment might not prove effective, with predictable unfavourable outcome.

One of the aims of the present invention is the description of some antimycotic agents exhibiting limited toxicity, negligible side-effects and simple administration in both hospital and at home.

This and other aims evidenced by understanding of the present description are attained by the complexes subject of the present invention.

In the course of studies on this new antibiotic, SPA-S-753, the possibility was demonstrated of complexing it with several substances of biological interest (liposomes, lipids, etc.), and in particular, it was surprisingly found that its complexation, or that of other salts or of its free base, with cholesterol 3-sulphate gives rise to a product presenting remarkable advantages from the therapeutic point of view.

These complexes were in fact found as effective, from the viewpoint of the in vitro microbiological activity, as the non-complexed active ingredient (SPA-S-753) against several pathogenic microorganisms, revealing, at the same time, an unexpectedly lower toxicity such as to ensure easier clinical application at higher doses, and fewer side effects in hospital and at home. A heightened therapeutic index is therefore observed which is of great practical interest, specially in consideration of the prominent mortality rate of these affections and of their ever expanding diffusion.

Moreover, the complexes obtained show biological activity higher than that of the antibiotic presently most used in therapy, that is, Amphotericin B.

The complexes subject of the present invention not only permit a more effective prophylactic and therapeutic action against mycotic infections, of which they reduce mortality, but also, thanks to their fewer side effects and reduced toxicity, allow easier and less costly treatment at home.

A specially important aspect of the new complexes, unlike uncomplexed SPA-S-753, is the fact that lesser precipitation is observed, and, at adequate doses, no precipitation occurs at the site of injection, e.g., after intramuscular administration. This translates itself in much better tolerance, in both systemic and local sense.

The complexes subject of the present invention ensure high and persistent blood levels—and surprisingly enough—lesser concentration and accumulation in certain target organs such as the kidneys, in the course of acute and continue treatments; it is this, a valuable advantage in the case of drugs, such as the polyene antibiotics, well known for their nephrotoxic effects.

The in vitro efficacy of the new complex along with its favourable pharmacokinetic characteristics were fully confirmed by in vivo tests performed in *C. albicans* experimentally infected mice treated by i.v. route with the drug in question, which was in fact demonstrated to possess high therapeutic efficacy with survival of all the animals and sterilisation of the infected foci.

ACUTE TOXICITY TEST (i.v. Administration in Mice)

Groups of 5 Sprague-Dawley male mice, of 4 weeks of age and weighing 14–18 g, starved overnight before trial, were treated with serial doses of the SPA-S-753-cholesterol sulphate complex (prepared as described in Example 1) and with the not complexed SPA-S-753 for comparison. The two products, dissolved in 5% glucose solution and diluted to the required concentrations, were injected by i.v. route into a tail vein, at a constant volume of 2 ml/kg and over the time of 30–40 seconds. The animals were then kept under observation for 15 days, while changes in behaviour and mortality were recorded. Data interpolation and calculations according to the Probit method gave an acute toxicity index of the substances, as lethal dose in 50% of the animals (LD50), of 46–64 mg/kg in the case of SPA-S-753 and of 120–180 mg/kg in the case of the SPA-S-753-cholesterol sulphate complex.

PHARMACOKINETICS TEST (i.v. Administration in Mice)

Two groups of 5 Sprague-Dawley male rats were treated by i.v. route with a single dose equivalent to 1.25 mg/kg of SPA-S-753-cholesterol sulphate complex and of not complexed SPA-S-753 for comparison, with a method similar to that described above. 2 hours following treatments the animals were killed, and the serum and kidneys were collected according to the ordinary procedures. The antibiotic was determined by the microbiological method on the pooled serums and organ homogenates from the 2 groups, the *Saccharomyces cerevisiae* growth inhibition zones being measured against those produced by antibiotic standard solutions (PYG-agar medium, incubation of 18 h at 30° C.). The antibiotic concentrations found were as follows: 2.6 $\mu$g/ml in serum and 4.0 $\mu$g/g in the case of SPA-S-753 alone, and 2.4 $\mu$g/ml in serum and 0.8 $\mu$g/g in the kidneys in the case of SPA-S-753-cholesterol sulphate complex.

The complexes subject of the present invention exhibit therefore increased efficacy in vivo, in the clinical practice, with a definite improvement as regards the health of patients presenting systemic mycoses (less frequent and milder side effects, increased survival rate) improved patients' compliance (fewer side effects, treatment at home rather than in hospital), decreased costs to be borne by the community (treatment at home rather than in hospital).

The complexes subject of the present invention contain N'-dimethylaminoacetylpartricin A dimethylaminoethylamide, as a salt or as the free base, and cholesterol 3-sulphate in a molar ratio varying from 1:0.5 to 1:10 respectively, preferably from 1:0.5 to 1:4.

Examples of pharmaceutically acceptable salts are the diaspartate (SPA-S-753), the diascorbate (SPA-S-843), the diglucuronate and the diglutammate.

Formation of the complexes can be achieved by any method apt to react the two ingredients under conditions of sufficient reactivity, such as, for instance, by combining, under stirring, the solutions of the two individual ingredients, in water or in organic solvents.

To be administered to patients the complexes may be formulated with suitable excipients and/or vehicles (diluents, disintegrating agents, dispersants, thickeners, pH regulators, isotonicity regulators, cryoprotective agents etc.) suitable to obtain stable pharmaceutical forms.

To preserve the samples various measures could be used, such as freezing and drying (e.g., by lyophilisation) or by other methods suitable to the purpose, of the complexes as such, or formulated with all or part of the ingredients making up the final pharmaceutical form.

Thanks to their antimycotic activity, the complexes subject of the present invention are useful in the treatment of mycotic infections in man, as well as in animals.

The quantity of the complex subject of the present invention, having an effective antimycotic action, is generally of 0.05 to 5 mg of active ingredient per kg of body weight, preferably between 0.1 and 1 mg per kg of body weight and depends, in general, on the administration route selected, by the patient's conditions and by the nature and gravity of the pathology.

The invention includes in its scope pharmaceutical compositions comprising one complex subject of the invention in combination with a pharmaceutically acceptable excipient (which may be a diluent or a vehiculating agent).

The nature of the compositions subject of the present invention will naturally depend on the administration route selected.

Their administration could be by oral, respiratory, rectal or parenteral routes even though the parenteral route is to be preferred. Parenteral administration may be intravenous, intramuscular, intra-arterial, subcutaneous, intraperitoneal, intrathecal, intralymphatic or intrapleural, even though intravenous and intramuscular administrations are to be preferred.

The compositions subject of the invention may be formulated in the accustomed forms, using common pharmaceutical ingredients.

The following examples are given merely for illustrative purposes and do not limit the scope of the present invention.

EXAMPLE 1

Prepare a solution (A) of 0.418 g of SPA-S-753 in 30 ml of distilled water, a solution (B) of 0.132 g of cholesterol 3-sulphate sodium salt in 30 ml of absolute ethanol, and a solution (C) containing tris buffer 1.212 g, EDTA bisodium 0.007 g, HCl q.s. at a pH 7.3 in 200 ml of distilled water. Add solution A to solution B under stirring: note the immediate formation of the colloidal dispersion of the SPA-S-753-cholesterol 3-sulphate complex. To the dispersion add 180 ml of solution C and therein dissolve, while shaking, 4.5 g of lactose monohydrate.

Distribute the colloidal dispersion in glass vials, in the amount of 4 ml per vial. Lyophilise, apply stopper and sealing rim. The colloidal dispersion immediately reforms following the extempore addition of distilled water.

EXAMPLE 2

Prepare a solution (A) of 0.836 g of SPA-S-753 in 60 ml of distilled water and a solution (B) of 0.264 g of cholesterol 3-sulphate in 60 ml of absolute ethanol. Add solution A to solution B under stirring: note the immediate formation of the colloidal dispersion of the SPA-S-753-cholesterol 3-sulphate complex. To the dispersion add 360 ml of distilled water and 9 g of lactose monohydrate.

Distribute the colloidal dispersion in glass vials, in the amount of 4 ml per vial. Lyophilise, apply stopper and sealing rim. The colloidal dispersion immediately reforms following the extempore addition of distilled water.

EXAMPLE 3

Prepare a solution (A) made up of 0.372 g of SPA-S-753 and 4 g of lactose monohydrate in 133 ml of distilled water, and a solution (B) of 0.123 g of cholesterol 3-sulphate in 26.7 ml of absolute ethanol. Slowly add solution B to solution A under brisk stirring: note the immediate formation of the colloidal dispersion of the SPA-S-753-cholesterol 3-sulphate complex. Distribute the colloidal dispersion in glass vials, in the amount of 4 ml per vial. Lyophilise, apply stopper and sealing rim. The colloidal dispersion immediately reforms following the extempore addition of distilled water.

EXAMPLE 4

Prepare a solution (A) made up of 0.372 g of SPA-S-753 and 4 g of lactose monohydrate in 133 ml of distilled water;

to it add 0.372 g of sodium ascorbate as an antioxidant and a solution (B) made up of 0.123 g of cholesterol 3-sulphate in 26.7 ml of absolute ethanol.

Proceed as described in Example 3, resulting in the desired complex in the form of a lyophilised powder. The colloidal dispersion immediately reforms following the extempore addition of distilled water.

EXAMPLE 5

A solution (A) of N'-dimethylaminoacetyl-partricin A dimethylaminoethylamide diascorbate (SPA-S-843), a solution (B) of cholesterol-3-sulphate sodium salt and a solution (C) of TRIS buffer and EDTA bisodium are reacted as described in Example 1, resulting in the desired complex in the form of a lyophilised powder.

What is claimed is:

1. A complex containing N'-dimethylaminoacetyl-partricin A dimethylaminoethylamide, as a salt or as the free base, and cholesterol 3-sulphate, in a molar ratio between 1:0.5 and 1:10, respectively.

2. A complex according to claim 1, wherein the salt is selected from the group consisting of the diaspartate, the diascorbate, the diglucuronate and the diglutammate.

3. A complex according to claim 1, wherein said molar ratio is between 1:0.5 and 1:4.

4. A pharmaceutical composition comprising a pharmaceutically suitable excipient and a complex according to claim 1.

5. A method of preparing the complex of claim 1, comprising combining the N'-dimethylaminoacetylpartricin A dimethylaminoethylamide and the cholesterol 3-sulphate, wherein the N'-dimethylaminoacetylpartricin A dimethylaminoethylamide is a salt or a free base.

6. A method of treating systemic mycotic infections, comprising administering an effective amount of the complex of claim 1 to a human or an animal in need thereof.

7. A process of treating systemic mycotic infections, comprising administering an effective amount of the complex of claim 2 to a human or an animal in need thereof.

8. A process of treating systemic mycotic infections, comprising administering an effective amount of the complex of claim 3 to a human or an animal in need thereof.

* * * * *

UNITED STATES PATENT AND TRADEMARK OFFICE
CERTIFICATE OF CORRECTION

PATENT NO. : 6,143,726
DATED : November 7, 2000
INVENTOR(S) : Tiberio Bruzzese, et al.

It is certified that error appears in the above-identified patent and that said Letters Patent is hereby corrected as shown below:

On the title page, Item [73], the Assignee's Residence is listed incorrectly. Item [73] should read as follows:

[73] Assignee: Quatex N.V., Curaçao, Netherlands Antilles

Signed and Sealed this

Twenty-ninth Day of May, 2001

Attest:

NICHOLAS P. GODICI

*Attesting Officer*   *Acting Director of the United States Patent and Trademark Office*